United States Patent [19]

Ruotoistenmäki et al.

[11] Patent Number: 5,662,626
[45] Date of Patent: Sep. 2, 1997

[54] PLASTER ACTING AS A DOSING DEVICE

[75] Inventors: Jussi Matias Ruotoistenmäki; Juhana Ruotoistenmäki, both of Helsinki; Jouko Artturi Nyman, Hyvinkää, all of Finland

[73] Assignee: Diomedes Oy, Helsinki, Finland

[21] Appl. No.: 525,759

[22] PCT Filed: Mar. 23, 1994

[86] PCT No.: PCT/FI94/00107

§ 371 Date: Sep. 22, 1995

§ 102(e) Date: Sep. 22, 1995

[87] PCT Pub. No.: WO94/21322

PCT Pub. Date: Sep. 29, 1994

[30] Foreign Application Priority Data

Mar. 23, 1993 [FI] Finland ............................. 931285
Mar. 22, 1994 [FI] Finland ............................. 941336

[51] Int. Cl.⁶ .................... A61F 13/00; A61F 13/02
[52] U.S. Cl. ............................. 604/306; 604/307
[58] Field of Search .................. 604/289, 290, 604/306, 307; 424/435, 434, 447–449; 128/155, 156

[56] References Cited

U.S. PATENT DOCUMENTS 3,874,387 4/1975 Barbieri ........................ 604/307
4,224,491 9/1980 Stiuala .
4,775,372 10/1988 Wilberg .
4,808,172 2/1989 Murata .
5,141,750 8/1992 Lee et al. .

FOREIGN PATENT DOCUMENTS

| 0081438 | 6/1983 | European Pat. Off. . |
| 0107575 | 2/1984 | European Pat. Off. . |
| 0107575 | 5/1984 | European Pat. Off. . |
| 3907007 | 9/1990 | Germany . |
| 4001380 | 7/1991 | Germany . |
| 560544 | 4/1975 | Switzerland . |

OTHER PUBLICATIONS

Search Report of PCT/FI94/00107.
WO90/05558.
WO90/07328.
WO91/08793.
WO93/00955.
WO91/03271.

*Primary Examiner*—John G. Weiss
*Assistant Examiner*—David J. Cho
*Attorney, Agent, or Firm*—Kane, Dalsimer, Sullivan, Kurucz, Levy, Eisele and Richard, LLP

[57] ABSTRACT

The objective of the invention is a new plaster and a method for delivering the substance to be dosed to the skin (11) through the attached plaster. The invention can be used for the administering of different ingredients to be dosed by plaster.

21 Claims, 4 Drawing Sheets

PLASTER ACTING AS A DOSING DEVICE

BACKGROUND OF THE INVENTION

1. Field of the Invention

The objective of the invention is a plaster which at the same time is a dosing device.

2. Description of the Prior Art

Different plasters are known. The simplest form of a plaster is a strip to be adhered onto the wound or other spot of treatment. The plaster can also be furnished with a gauze dressing, which can be filled (impregnated) with some suitable substance. By this a simple means is achieved for local (topical) treatment of an injury or simply for protection from external contamination.

In recent years, plasters applied with drugs and dosage devices have become all the more important in the administration of integrated active drugs. The integrated (systemic) dosing devices can be divided into two main groups. In the first group, the drug composition is contained in the adhesive or is impregnated into a suitable porous substance (membrane), which adhered to the skin starts delivering the active ingredient.

The other group comprises dosing devices, which usually contain a reservoir having a membrane as one wall through which the substance to be dosed is administered to the skin.

The above mentioned means are below presented illustrated by their patent publications.

Plasters, in which the drug is contained in the adhesive, or the drug is in a reservoir, which all over is covered by adhesive, or in which the drug is solved, or is contained in a fungous material through which it can be freely delivered, and in which the adhesive surrounds the contact layer between the reservoir and the patient but does not cover the contact surface, are described in the U.S. Pat. Nos. 3,598,122, 3,589,123, 3,731,683, 3,734,097, 3,742,951 and 3,797,494.

The FI applications 870 557 and 865 088 present a dermal or transdermal dosing system, in which beneath a substance impermeable top layer is a drug reservoir and a membrane, the surface of which facing the skin is adhered to the skin, leaving part of the membrane free for the dosing. The membrane is moreover surrounded by an adhesive slip, and the active ingredient is stored beneath the top layer. The WO 90/07328 publication presents an application device, in which the active ingredient is placed in a ring-shaped opening (chamber) inside the periphery underneath the top layer. In this model the top layer or part of it can be opened and closed and moreover the chamber can contain a membrane.

The WO 93/00955 publication presents a dosing device, having a separate bellows-like gear in the drug reservoir, which at increased temperature delivers the substance to be dosed through the membrane and performs the dosing through the wall formed of the chamber membrane.

In the CH 560 544 publication is presented a dosing device similar to the one described above, in which the active ingredient is in a reservoir having a membrane as one wall. The means can also contain a second chamber, the increase in volume of which leads to a decrease in the reservoir, and thus to an increased dosing. The ingredient to be administered can be added to the reservoir. The bandage is adhered to the skin from its edges 2 containing the adhesive agent.

The U.S. Pat. No. 4,224,941 publication presents a pressurized application device for skin treatment. The device is at rest folded and has under pressure a ball-shaped part. This hyberbaric device is used for treatment of a desired spot at a certain pressure.

The storage of some of the devices described above cause problems. The active ingredient of some of the devices is stored inside the membrane, by which it might concentrate in some part of the membrane. Some devices have to be stored in a certain position. The membrane of some devices might in use come off the skin, and the adhesive area of some adhered membranes reduces the treatment area. The use of some active ingredients restricts the amount of adhesives. Some devices requires filling of the active ingredient after the attachment. The adhesion-drug contact of some devices is continuous. The dosage of some of the devices described above resembles oral administration illustrated by the time-dose diagram and cannot be changed. Some devices are not suitable for home treatment.

SUMMARY OF THE INVENTION

The objective of the invention is to achieve a decisive improvement of the above mentioned disadvantages. For the embodiment of this the device according to the invention is characterized in what is presented in the claims.

The device according to the invention, having two or several chambers, is adapted for the dosing of solutions and pastes onto the skin. The active ingredient is stored in a closed reservoir, called store chamber. From the store chamber the ingredient is brought to use through a connecting channel to the dosing space, having the top layer as one wall and the skin as the other wall. During storing, the connecting channel is closed. The dosing chamber is sealed by at least one threshold directed towards the skin, while the purpose of the outermost threshold, in addition to sealing, is to prevent the contact between the adhesive and the active ingredient. The device is applied to the skin either by adhering with the fixing means, or by using a strap fixing. The storing takes place in a store reservoir, from which the connection is closed to the dosing space during storage.

BRIEF DESCRIPTION OF THE DRAWINGS

The invention is below described with reference to the enclosed drawings, in which.

DESCRIPTION OF THE PREFERRED EMBODIMENTS

Figure 1:
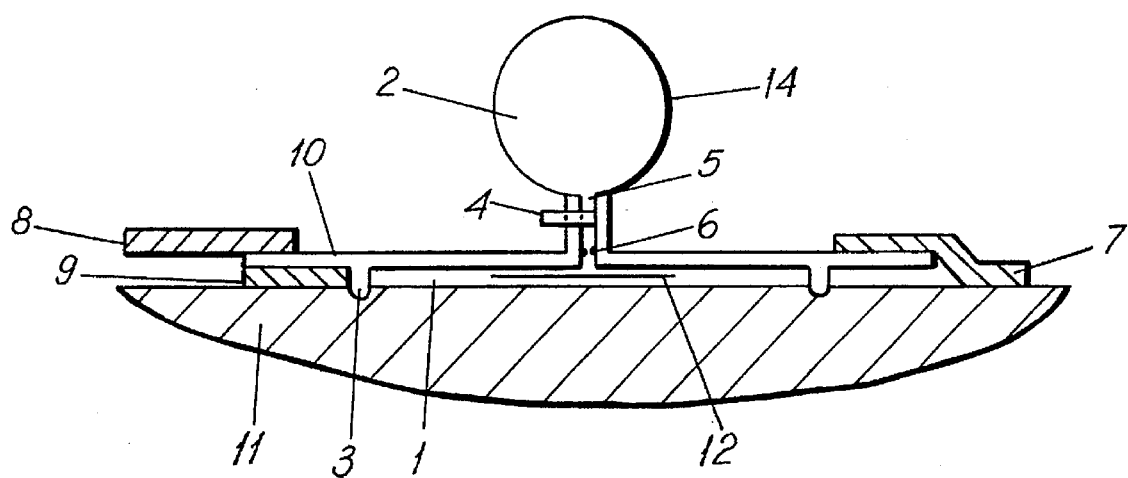
FIG. 1 is a cross-section of the plaster from the side.

FIG. 1 presents a cross-section of the plaster from the side. The plaster consists of the dosing department 1, which is an intermediate space between the film 10 and the skin 11. From the edges it is restricted by thresholds or projections 3, that seal the film 10 onto the skin 11. From the dosing department 1, there is connection via the connecting channel 5 to the store reservoir 2, from which the ingredient can be dosed to the dosing reservoir 1. The reservoir 2 can be according to the figure or implemented substantially more flat like the dosing department 1. The plaster can be attached to the skin by different fixing means. The fixing means can be attached on top 7 of the film 10 or underneath 9 it (between the film and the skin), or the fixing means can be a fixing strap 8 attached to the film. The connecting channel 5 can in non-use be furnished with a tear-off protective tape 12, thus protecting also the adhesive layers of the fixing means of the plaster or bandage.

The active ingredient is stored in the store reservoir 2, and in use the desired amount is dosed through the connecting channel 5 to the dosing department 1, i.e. the store space and the dosing space contain the same ingredient. The threshold 3 can be made of non-deformable material. The part of the threshold that comes against the skin, can be rounded. The threshold prevents the possible adhesive and the ingredient to be dosed from coming into contact with each other. When there are several thresholds, these can divide the dosing space into several sections.

Figure 4:
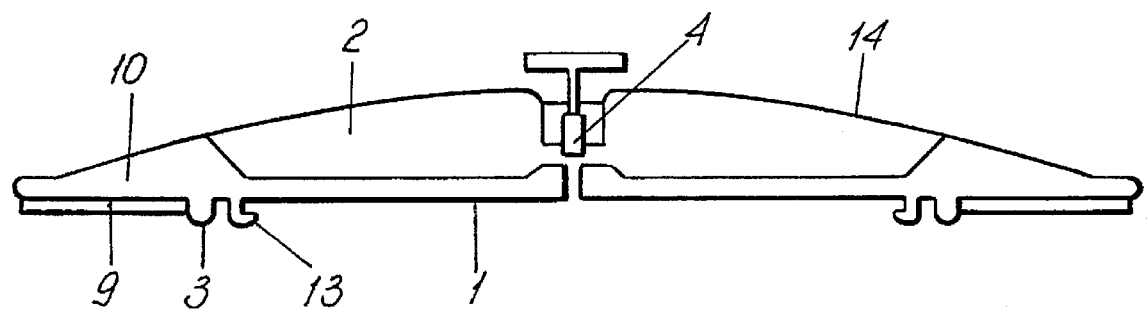
FIG. 4 presents an embodiment of the plaster with one dosing reservoir and two store reservoirs.

Several sealing thresholds can also be used. The innermost threshold 3 of the dosing chamber can be shaped so that the innermost edge 13 of the threshold (FIG. 4) operates as fixing threshold of a possible membrane and the membrane can also contain thresholds. The edge of the threshold 3 can be furnished with a projection 13 placed substantially in the film direction for the fixing of a possible membrane. From the different store departments there can be separate connecting channels between each dosing reservoir and store reservoir.

This enables e.g. dosing of a different ingredient in the innermost section than in the outermost section of the dosing department 1 either concentrically or asymmetrically. The same device can contain dosing departments of different volume. There can be several store reservoirs for storing different ingredients, each reservoir having then its own connecting channel to e.g. a common dosing reservoir, where e.g. the ingredients can be mixed. This enables a longer storage of the ingredients.

In the connecting channel 5, the substance to be dosed can go in either direction.

The store reservoir 2 or at least a part of its wall 14, can be so formed that the volume of the chamber can be reduced by e.g. pressing, or increased, by which these measures either increase or decrease the administration on the skin, i.e. they cause the filling or emptying of the dosing department. For the dosing, the connecting channel 5 can also be furnished with a nozzle 6, to control the dosing.

Figure 5:
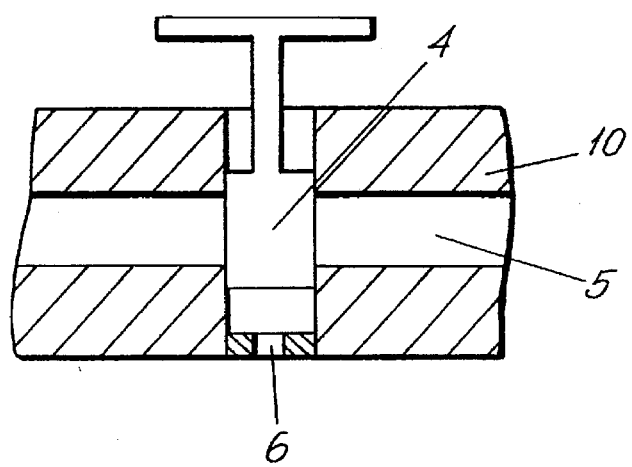
FIG. 5 is an enlargement of the valve shown in FIG. 4.

The opening of the connecting channel 5 can be equipped with a valve (nozzle), e.g. a hose choker, or a plug, to prevent the exit of the substance from the dosing department 1. The plaster stays fixed to the skin with the adhesive. Before applying the plaster, the adhesive layer of the plaster and the opening of the connecting channel are protected by a protective film 12 in a normal way. FIG. 5 presents one example of a valve in an application with two store reservoirs.

The film and the adhesive agent is manufactured of suitable materials for each case. The film properties can be different in different applications of use. The same plaster can have two or several films, the films can be of different shapes in the same plaster. The substances to be dosed, which together can go bad quickly, can be mixed only in the dosing chamber when the plaster is being used. There can then be e.g. two or several store reservoirs containing different substances, e.g. in cases of cortisone ointments.

The adhesive bond to fix the plaster is simplest a peripheral film edge outside the threshold, with an adhesive layer on the surface that comes towards the skin. It can also be of different shape than the film.

Figure 2:
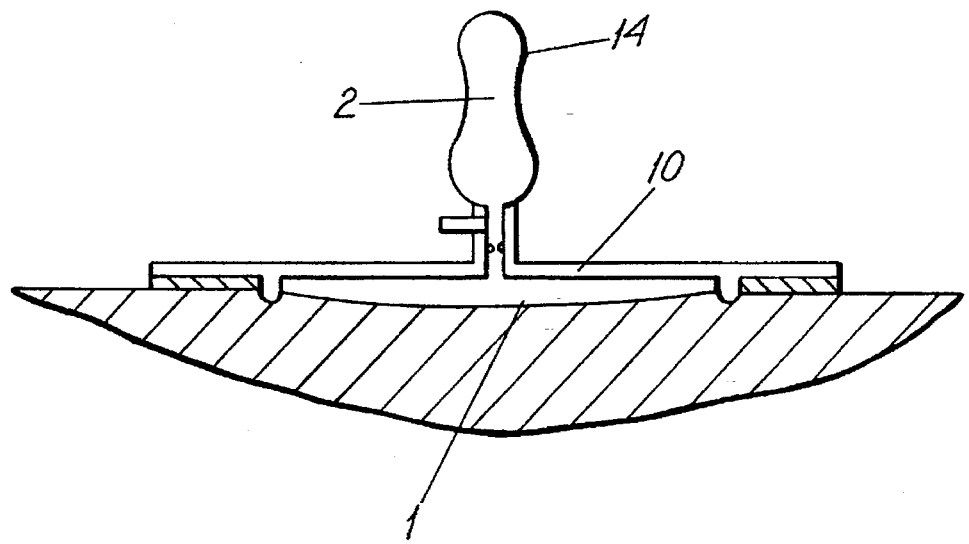
FIG. 2 is a cross-section of the plaster from the side during dosing.

In FIG. 2 the outermost film section 14 has been compressed and the substance has flown to the dosing space 1 between the innermost film 10 and the skin 11. The whole store reservoir 2 or part of its wall 14, can be made of a flexible material, by which pressing the wall or the bellows-like gear creates a dosing pressure. The store chamber can also be filled so that the chamber or some part of the wall expands during the filling. The so created unpressurized or pressurized departments 2 can be preserved for later use. The valve 4 in the connecting channel 5 closes the store space, by which the possible pressure and the active ingredient are in a closed space inside the store reservoir 2. The substance becomes accessible by opening the valve 4. The flow rate of the substance can be affected by opening the valve and by the store space pressure.

The connecting channel 5 can also have a nozzle 6 to control the flow rate. As a nozzle can function the whole channel opening "choker portion" (nozzle) or a valve in the channel. With the above means a desired dosing illustrated by the time-dose diagram can be achieved. The dosing can be made even or pulsing, it can be interrupted or the bellows-like gear can even be used to empty the dosing chamber. There can be one or several connecting channel openings. The valve or the like can control e.g. speed, quantity or direction of the ingredient to be dosed.

Figure 3:
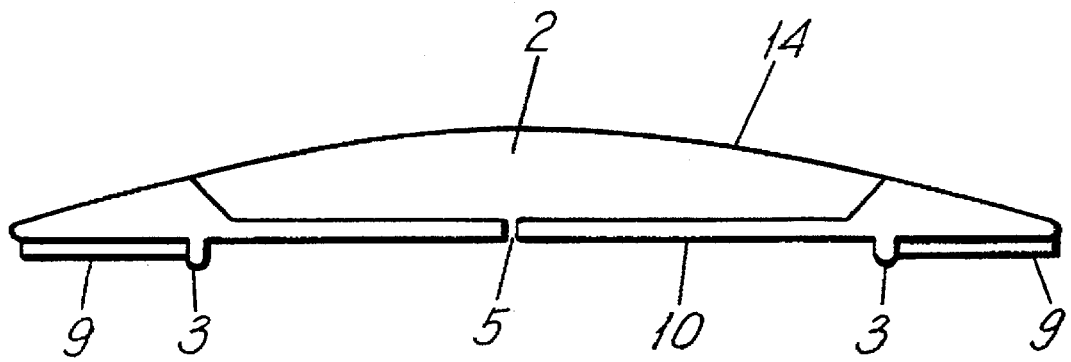
FIG. 3 is a flat embodiment of the plaster.

FIG. 3 presents a more flat embodiment of an at least two-chamber device, in which the films on top of each other are in the skin direction. Also in this embodiment, the store chamber 2 can be pressurized when filling or a dosing pressure can be created by pressing the film 14. The film 14 can be protected by a special protective film. In embodiments with several store reservoirs, these can be emptied at different times if desired.

Figure 6:
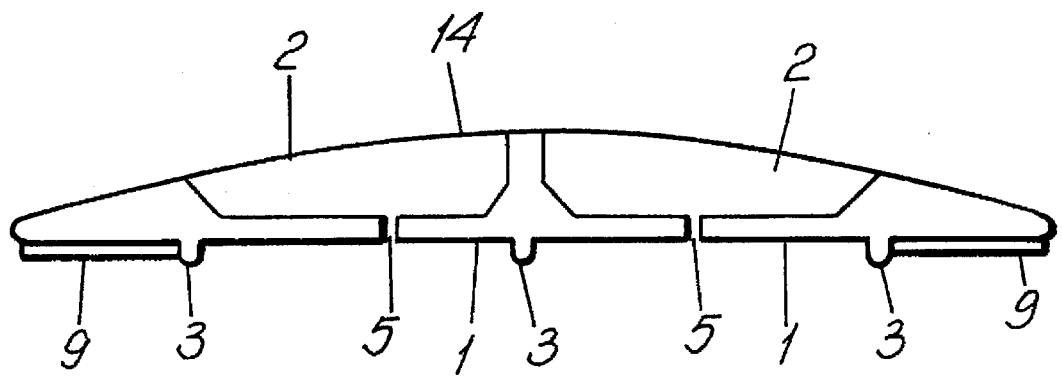
FIG. 6 is a profile of the plaster in which the store and the dosing spaces have been divided into sections.
Figure 7:
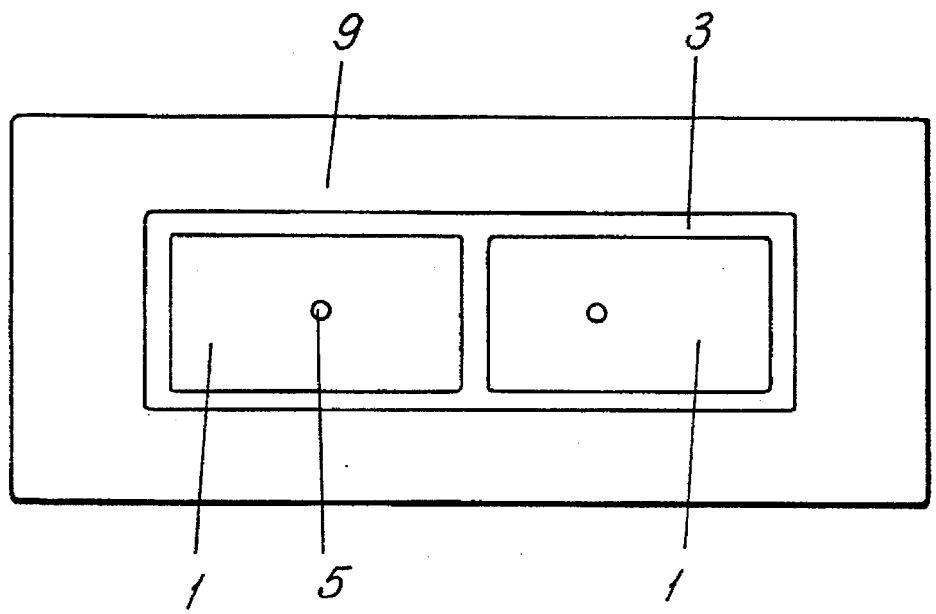
FIG. 7 is the plaster according to FIG. 6 presented from underneath.

In FIG. 6, the store and dosing spaces 2 and 1 are divided into sections by the threshold 3 in embodiments with two connecting channels and two store and two dosing spaces. The connecting channel can thus be formed of e.g. two or several parallel openings or a slit-shaped opening. FIG. 7 presents the same plaster from underneath.

Figure 8:
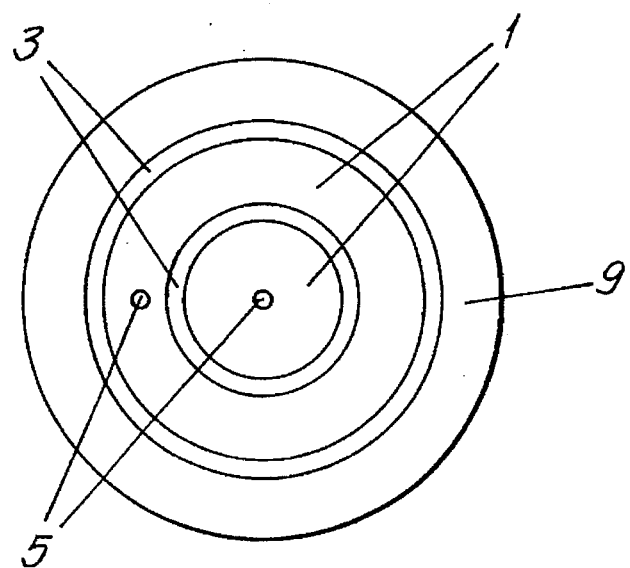
FIG. 8 presents another embodiment from underneath.

FIG. 8 presents an additional embodiment of the plaster, in which the dosing spaces have been divided into sections by ring-shaped thresholds. From the connecting channels there is a connection to the desired store space.

The plaster comprises a store space as well as a dosing space, with a connection between them. The connection can be closed. The feeding of the substance to be dosed can be controlled through the connection. The substance to be dosed is stored in the plaster store space before use. The substance can be stored in more than one reservoir, by which the store reservoir is divided into sections by partitions. Each reservoir can be in contact with the dosing space. The dosing space is restricted by walls, which prevent the contact between the ingredient to be dosed and the adhesive.

The parts of the dosing device are:
1 Dosing chamber
2 Store chamber
3 Threshold
4 Valve
5 Connecting channel
6 Nozzle
7 Fixing means, on top of the film
8 Fixing means, strap
9 Fixing means, between film and skin
10 Film
11 Skin 12 Protective tape
13 Threshold edge for fixing the membrane
14 A second film

We claim:

1. A plaster to be attached to the skin, having a film (10) impermeable to an active ingredient, which film contains a fixing means (7, 8, 9) for the attachment of the plaster, by which the plaster is attached to a desired spot tightly and without permeating the active ingredient, characterized in that on the one side of the film (10) there is at least one store chamber (2) and on the other side at least one dosing chamber (1) for the active ingredient, with thresholds (3) on at least peripheral edges of said dosing chamber (1) directed from the film (10) towards the skin to prevent the plaster from coming in contact with the active ingredient in the dosing chamber, at least one connecting channel (5) between the store and the dosing chambers (2,1) and at least one valve (4) in said at least one connecting channel (5).

2. The plaster according to claim 1, characterized in that each store chamber (2) has its own connecting channel (5) to the corresponding dosing chamber (1).

3. The plaster according to claim 2, characterized in that the store chambers (2) are connected with the dosing chamber (1) through one connecting channel (5).

4. The plaster according to claim 3, characterized in that the thresholds (3) have been placed to divide the dosing chamber into sections, while the thresholds (3) on the peripheral edges of said dosing chamber prevent contact between said plaster and said active ingredient.

5. The plaster according to claim 4, characterized in that the edge of the threshold (3) has been furnished with a projection (13) placed substantially in the film direction.

6. The plaster according to claim 5, characterized in that the motion of the substance to be dosed can be controlled in the connecting channel (5).

7. The plaster according to claim 6 characterized in that the plaster comprises two or several store chambers (2), having different ingredients, which can be mixed in at least one of the dosing chamber (1) and the connecting channel (5).

8. The plaster according to claim 7, characterized in that the store chambers (2) are placed on top of each other.

9. The plaster according to claim 7, characterized in that adjacent chambers (2) are divided into sections.

10. The plaster according to claim 7, characterized in that the connecting channel (5) is protected by a cover (12).

11. A plaster to be attached to the skin, having a film (10) impermeable to an active ingredient, which film contains a fixing means (7, 8, 9) on the film for the attachment of the plaster, by which the plaster is attached to a desired spot tightly and without permeating the active ingredient, characterized in that on the one side of the film (10) there is at least one store chamber (2) and on the other side at least one dosing chamber (1) for the active ingredient, with thresholds (3) on at least peripheral edges of said dosing chamber (1) directed from the film (10) towards the skin to prevent the plaster from coming in contact with the active ingredients in the dosing chamber, at least one connecting channel (5) between the store and the dosing chambers (2, 1) so that the store chambers (2) are connected with the dosing chamber (1) through one connecting channel (5), and the thresholds (3) have been placed to divide the dosing chamber into sections, while the thresholds (3) on the peripheral edges of said dosing chamber prevent contact between said plaster and said active ingredient.

12. A plaster to be attached to the skin, having a film (10) impermeable to an active ingredient, which film contains a fixing means (7, 8, 9) on the film for the attachment of the plaster, by which the plaster is attached to a desired spot tightly and without permeating the active ingredient, characterized in that on the one side of the film (10) there is at least one store chamber (2) and on the other side at least one dosing chamber (1) for the active ingredient, with thresholds (3) on at least peripheral edges of said dosing chamber (1) directed from the film (10)1 towards the skin to prevent the plaster from coming in contact with the active ingredient in the dosing chamber, at least one connecting channel (5) between the store and the dosing chambers (2, 1)so that each store chamber (2) has its own connecting channel (5) to each corresponding dosing chamber (1), and the thresholds (3) have been placed to divide the dosing chamber into sections, while the thresholds (3) on the peripheral edges of said dosing chamber prevent contact between said plaster and said active ingredient.

13. The plaster according to claim 12, characterized in that the edge of the thresholds (3) have been furnished with a projection (13) placed substantially in the film direction.

14. The plaster according to claim 13, characterized in that there is a valve (4) in the connecting channel (5).

15. The plaster according to claim 14, characterized in that the motion of the substance to be dosed can be controlled in the connecting channel (5).

16. The plaster according to claim 15, characterized in that the plaster comprises two or several store chambers (2), having different ingredients, which can be mixed in the dosing chamber (1) in the connecting channel (5).

17. The plaster according to claim 16, characterized in that the store chambers (2) are placed on top of each other or that the adjacent chambers (2) are divided into sections by partitions and/or that the connecting channel (5) is protected by a cover (12).

18. The plaster according to claim 16 characterized in that adjacent chambers (2) are divided into sections.

19. The plaster according to claim 16 characterized in that the connecting channel (5) is protected by a cover (12).

20. A plaster to be attached to the skin, having a film (10) impermeable to an active ingredient, which film contains fixing means (7, 8, 9) for the attachment of the plaster, by which the plaster is attached to the desired spot tightly and without permeating the active ingredient, characterized in that on the one side of the film (10) there is at least one store chamber (2) and on the other side at least one dosing chamber (1) for the active ingredient, at least one connecting channel (5) between the store and the dosing chambers (2,1), and thresholds (3) on at least peripheral edges of said dosing chamber (1) directed from the film (10) towards the skin to prevent the plaster from coming in contact with the active ingredient in the dosing chamber where the thresholds (3) on at least the peripheral edges of said dosing chamber (1) are furnished with a projection (13) placed substantially in the film direction.

21. A method for dosing the substance to be dosed through a plaster, in which method the plaster is adhered to the desired spot by fixing means (7, 8, 9) substantially tightly to the skin and without permeating the substance to be dosed, which plaster contains a film (10), which from underneath restricts the dosing chamber (1), characterized in that said method comprising the step of delivering the substance to be dosed from the store chamber (2) on top of the film (10) to the dosing chamber (1) restricted by thresholds (3) projecting towards the skin through the connecting channel (5) between the chambers (1, 2) to prevent the plaster from coming in contact with the active ingredient in the dosing chamber.

* * * * *